United States Patent [19]

Nakashima et al.

[11] 4,171,283

[45] Oct. 16, 1979

[54] HEMOPERFUSION ADSORBENTS

[75] Inventors: Toshihide Nakashima, Kurashiki; Koichi Takakura, Okayama, both of Japan

[73] Assignee: Kuraray Co., Ltd., Kurashiki, Japan

[21] Appl. No.: 820,380

[22] Filed: Jul. 29, 1977

[30] Foreign Application Priority Data

Aug. 4, 1976 [JP] Japan .................................. 51-93746
Sep. 24, 1976 [JP] Japan ................................ 51-114092
Feb. 18, 1977 [JP] Japan .................................. 52-17394

[51] Int. Cl.$^2$ ............................................ B01D 11/04
[52] U.S. Cl. ................................. 252/428; 252/426; 252/430; 210/22 C; 210/24; 210/502; 128/214 R
[58] Field of Search ................... 252/426, 428, 430; 210/22, 24, 502; 128/214 R

[56] References Cited

U.S. PATENT DOCUMENTS

| | | | |
|---|---|---|---|
| 3,794,584 | 2/1974 | Kunin | 210/22 X |
| 3,983,053 | 9/1976 | Courtney et al. | 252/428 X |
| 4,076,892 | 2/1978 | Fennimore et al. | 252/426 X |

OTHER PUBLICATIONS

Andrade et al., Amer. Soc. Artif. Int. Organs, vol. 17, (1971), pp. 222–228.
Andrade et al., Amer. Soc. Artif. Int. Organs, vol. 18, (1972), pp. 473–485.

Primary Examiner—Patrick Garvin
Attorney, Agent, or Firm—Barry Kramer

[57] ABSTRACT

A hemoperfusion adsorbent is provided comprising an adsorbent material containing at least one coating thereon of a hydrophilic polymer prepared by the polymerization of at least one monomeric acrylate or methacrylate with a copolymerizable monomer containing an epoxy moiety therein.

In addition, a method is provided for removing air bubbles from such adsorbents comprising boiling said adsorbents in water or physiological saline, cooling said adsorbents, packing said adsorbents into a container and sterilizing the packed container by autoclaving.

7 Claims, No Drawings

HEMOPERFUSION ADSORBENTS

This invention relates to adsorbents for hemoperfusions. More particularly, the invention relates to a hemoperfusion adsorbent characterized in that it has a coating layer comprising a hydrophilic copolymer of an acrylate or methacrylate and a copolymerizable monomer containing an epoxy moiety.

It is known that removal of exogenic and endogenic toxins from the blood is effective for the treatment of intoxication, hepatic coma due to acute or chronic hepatic failure, renal failure, etc. Hemodialysis has been commonly employed for such purposes. More recently, attempts have also been made to bring the blood or plasma into direct contact with an adsorbent such as activated carbon or anion exchange resin and thereby adsorb and remove such toxins. Hemoperfusion adsorbents of such direct contact type are preferably such that they are least liable to induce clotting, hemolysis, reduction in platelet counts, denaturation of blood components or the release of micro-particles from the adsorbents. However, insofar as adsorbents are directly contacted with the blood or plasma, it is difficult to obviate such disadvantages altogether. To overcome these problems, J. D. Andrade et al., Trans. Am. Soc. Artif. Intern. Organs 18, 473(1972) has found that coating such adsorbents with a water-insoluble and hydrophilic polymer such as poly(hydroxyethyl methacrylate) is particularly effective. The coating layer composed of such a polymer is superior to the conventional coatings of gelatin, collodion, albumin or the like heretofore employed, particularly with respect to compatibility with the blood, and offers the advantages of reduced incidences of clotting, hemolysis, reduction in platelet counts, denaturation of blood components, etc., in addition to its lack of immunogenicity.

Because of its hydrophilic nature, the coating of the aforesaid hydrophilic polymer has excellent blood compatibility and this property makes an adsorbent having such a coating a superior material in the sense that it overcomes the aforementioned disadvantages due to direct contact with the blood. However, the mechanical weakness of the coating layer in water due to the hydrophilic nature thereof, can cause peeling of the coating layer from the adsorbent to some extent.

While use of the hydrophilic polymer is highly desirable due to its superior biocompatibility, prior efforts to prevent peeling of the coating from the adsorbent have not been successful. Thus, for example, it has been heretofore proposed to incorporate a suitable bifunctional monomer or a cross-linking agent in the coating solution and to subject the coated adsorbent to a heat treatment so as to effect cross-linking. The possibility remains, however, with this method, that unreacted monomer or cross-linking agent could reside in the coating layer and thus, be released into the blood during use of the adsorbent.

Accordingly, it is an object of this invention to provide improved hemoperfusion adsorbents.

It is another object of this invention to eliminate the disadvantages associated with prior hemoperfusion adsorbents.

These as well as other objects and advantages are accomplished in accordance with the present invention by providing hemoperfusion adsorbents comprising an adsorbent having at least one coating thereon of a hydrophilic polymer prepared from at least one acrylate or methacrylate monomer and a copolymerizable monomer containing an epoxy moiety.

Through use of the hydrophilic polymer of the present invention, it is possible to improve the strength of the coating layer through a curing treatment after the coating operation, to preclude the formation of microparticles from the adsorbent itself and the coating layer and to avoid elution of the coating polymer (including low molecular weight polymer as well as unreacted monomer or cross-linking agents which are conventionally used to cross-link the polymer.)

The substrate adsorbent can be any conventionally employed adsorbent such as activated carbon, alumina, silica, ion exchange resins, and the like. The adsorbent particles are preferably those which are as free from protruding surfaces as possible, i.e. spherical or substantially spherical, for the purpose of precluding formation of microparticles and preventing clotting and hemolysis. When activated carbon is employed, bead carbon manufactured from petroleum pitch in the size range of 0.1 to 5 mm, more preferably about 0.5 to 1 mm dia., are desirable because they have high adsorptive capacities and low pressure drop. Thus, adsorbents manufactured by coating bead activated carbon with said hydrophilic polymer is a preferred embodiment of the present invention.

Other than as stated above, the shape of the adsorbent is not particularly important in the present invention. Thus, the adsorbent may be spherical, fibrous, flat, or may be an integrally shaped article having a continuous passageway or set of passages therethrough which permits flow of the blood.

The adsorbent coating produced from the hydrophilic polymer of the present invention has been found to exhibit good blood compatibility. The monomer employed as a principal component of said polymer is desirably one or more hydrophilic acrylates or methacrylates represented by the general formula:

$$CH_2=CR_1 \atop | \atop COO-Y \qquad (I)$$

wherein Y is a radical selected from the group consisting of $-R_2-OR_3$ and $-R_2-NR_3R'_3$, $R_1$ is hydrogen or methyl; $R_2$ is a divalent alkylene group of 2 to 3 carbon atoms or a poly (oxyalkylene) group, which can optionally be substituted; $R_3$ and $R'_3$, respectively, are hydrogen or an alkyl group of 1 to 3 carbon atoms which can optionally be substituted by polar groups such as hydroxyl, amino and the like.

Illustrative of such acrylate and methacrylate monomers are the substituted and unsubstituted hydroxy or alkoxyalkyl acrylates and methacrylates, amino or alkylamino acrylates and methacrylates, and the poly-(alkylene glycol) acrylates and methacrylates. More particularly, hydroxyethyl methacrylate, hydroxyethyl acrylate, hydroxypropyl methacrylate, hydroxypropyl acrylate, polyethylene glycol monomethacrylate, polyethylene glycol monoacrylate, polypropylene glycol monomethacrylate, polypropylene glycol monoacrylate, methoxyethyl methacrylate, methoxyethyl acrylate, dimethylaminoethyl methacrylate, dimethylaminoethyl acrylate and the like.

The polymerizable comonomer containing an epoxy moiety which is incorporated in the polymer to improve the strength of the coating and to prevent elution of the coating layer is a comonomer represented by the following general formula:

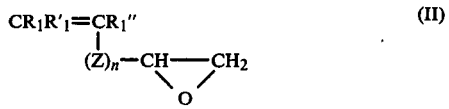

wherein Z is a divalent radical selected from the group consisting of —COO—$R_2$— and —$CH_2$—$OCH_2$—, n is 0 or 1, $R_1$, $R_1'$ and $R_1''$ are each, respectively, hydrogen or methyl and $R_2$ is a divalent alkylene radical of 1 to 3 carbon atoms or a poly(oxyalkylene) radical which optionally can be substituted.

Illustrative of such comonomers containing an epoxy moiety are glycidyl methacrylate, glycidyl acrylate, glycidyl crotonate, allylglycidyl ether, methallylglycidyl ether, butadiene monoxide, isoprene monoxide and the like.

In view of the ease of copolymerization with said hydrophilic acrylate and/or methacrylate monomers, glycidyl methacrylate and glycidyl acrylate are particularly preferred.

The hydrophilic polymers of the present invention can be produced by copolymerizing a predominant amount of monomer (I) with a minor amount of the epoxy-containing comonomer (II) in a solvent, e.g. methanol, ethanol (aqueous ethanol inclusive), or dimethylformamide, and in the presence of a free radical polymerization initiator such as azobisisobutyronitrile, diisopropyl peroxydicarbonate, tert-butyl peroctoate, benzoyl peroxide and the like at a temperature between 40° and 100° C. for several hours. The feed ratio of the epoxy-containing monomer is 0.1 to 10 percent, and preferably, 0.5 to 5 percent based on the weight of total monomers.

If the feed ratio of epoxy-containing monomer is less than 0.1 percent, the desired cross-linking effect will not be obtained; while if the feed ratio is in excess of 10 percent, gelation of the copolymer can occur during storage.

The resultant polymer is dissolved in a suitable solvent such as methanol, ethanol or aqueous ethanol and can be used to coat the adsorbent by dipping, spraying or wet coagulation. The concentration of the polymer in the coating solution is 0.01 to 10 percent and more preferably, 0.5 to 5 percent. The coating thus applied is dried by heating at 80°–120° C. for 1 to 24 hours, whereby the polymer constituting the coating layer cross-links to form a gel as the epoxy moieties react. This cross-linking reaction leads to an improved attrition resistance, a reduced incidence of micro-particle formation and further prevention of elution of the polymer by autoclaving. These effects can be further enhanced by repeating the above coating procedure two or more times. Where two or more coatings are applied, the coating materials need not be identical in composition but different coating compositions can be employed according to the intended use of the product.

As shown in the examples which appear hereinafter, the adsorbent having a coating layer thereon comprised of a hydrophilic polymer of the present invention containing epoxy moieties therein has an adsorptive capacity as high as that of similar uncoated adsorbents and that of adsorbents coated with hydrophilic acrylate or methacrylate polymer containing no epoxy groups. Notwithstanding this fact, the coated adsorbents according to this invention are able to adsorb and remove 99 percent and more of creatinine from a 0.2 g/1 aqueous solution in two hours. This is in contrast to coconut shell carbon which adsorbs only about 85 percent in 2 hours.

The results set forth in Table 1 below demonstrate that the coating of bead activated carbon with a hydrophilic acrylate or methacrylate copolymer containing epoxy moieties according to this invention significantly reduces the incidence of formation of micro-particles. It will also be apparent from Example 3, which appears hereinafter, that the amount of elution in the course of sterilization of the coated adsorbent of this invention is significantly less than that of the collodion-coated adsorbent. The coated adsorbent according to this invention can be sterilized by steam autoclaving as well as dry heat, a chemical sterilant such as ethylene oxide or formalin, and radiation.

In another aspect of the present invention, a method is provided by which the adsorbent can be successfully sterilized with steam autoclaving.

In accordance with the present invention, the adsorbent can be packed into a container under wet conditions together with water or physiological saline and sterilized by autoclaving. It has been found that air bubbles settle on the surface of the adsorbent and that these bubbles can hardly be removed by contact with water, physiological saline, blood or other fluid. Moreover, air bubbles have been found to form on the surface of the adsorbent even when the adsorbent is packed dry into a similar container and after heat sterilization, water or physiological saline is introduced into the container. These results are apparently due to the readiness of the adsorbent to adsorb air. Since air bubbles on the adsorbent not only lower its adsorptive capacity but also exert untoward effects upon the blood, such as hemolysis, clotting and denaturation of blood components, it is important to make every effort to substantially preclude the presence of air bubbles.

To prevent formation of air bubbles in the sterilization step, it would be preferable to accomplish sterilization by autoclaving in a wide-mouthed vessel such as a beaker. However, such practice is undesirable in that there is always the possibility of recontamination when the sterilized adsorbent is packed into the column through which the blood is to be passed.

It has now been found that the formation of air bubbles can be effectively prevented by first treating the adsorbent with boiling water or boiling physiological saline and, after cooling and packing it into a container, subjecting it to autoclave sterilization.

Thus, this invention further provides a method of sterilizing hemoperfusion adsorbents characterized in that said method comprises boiling the adsorbent in water, physiological saline or the like and, after cooling and packing into a container, subjecting it to autoclave sterilization.

By this boiling of the adsorbent in water or physiological saline in accordance with this invention, not only the dissolved gases in the liquid, but also any gases adsorbed on the adsorbent are expelled therefrom. Moreover, the water finds its way into the voids in the adsorbent so that no bubble formation will take place if the adsorbent is packed into a container and subjected to autoclave sterilization under sealed conditions.

Thus, the adsorbent is first boiled in water or physiological saline. In so doing, it is desirable to ensure that air bubbles will be freely driven out of the fluid. This boiling treatment can be conducted at atmospheric pressure, or can be conducted by heating the adsorbent in an autoclave at an elevated temperature of no less than 100° C.

After boiling, the adsorbent is cooled to a temperature which permits handling, i.e. normally room temperature, and is packed into a container. This container can be any type of vessel suited for the intended use. For example, it can be cylindrical, spindle-shaped or otherwise configured. The container can be made of any material that withstands wet heat sterilization at high temperature and will not release any physiologically harmful ingredients. The adsorbent is packed into such a container, in wet condition, and is then subjected to high-temperature sterilization by autoclaving. Sterilization is normally accomplished by the introduction of water vapor at a temperature of at least 120° C. The formation of air bubbles from the adsorbent is not observed during such procedure.

The sterilized container holding the adsorbent is closed gas-tight by a suitable means so that the adsorbent will be held in wet and sterile condition. In use, the blood is perfused through the container.

Since sterilization can be performed in a final stage of manufacture of the hemoperfusion column, the maximum advantage is realized with regard to safety.

It should be understood that the sterilization method of the present invention can be applied not only to the adsorbent of this invention but also to the prior art adsorbents such as adsorbents coated with collodion, cellulose acetate, nylon, polyurethane, silicone resin, gelatin, poly(hydroxyethyl methacrylate) and other high polymers.

The adsorbent according to this invention can be used in the direct adsorption of blood or the adsorption of the plasma separated by filtration or centrifugation, for the treatment of intoxication, hepatic coma, renal failure and other diseases.

The following examples are intended to illustrate this invention in further detail. In these examples, all parts and percentages are by weight unless otherwise indicated.

EXAMPLE 1 AND CONTROL EXAMPLES 1-3

A mixture of 95 parts of hydroxyethyl methacrylate, 5 parts of glycidyl methacrylate, 0.1 part of diisopropyl peroxydicarbonate and 700 parts of 95% ethanol was stirred at 60° C. in a nitrogen atmosphere for 8 hours. The resultant copolymer was dissolved in 95% ethanol to give a concentration of 0.5%. Bead activated carbon (BAC-MU.L, by Taiyo Kaken K.K.; particle diam. 0.40–0.84 mm; substantially spherical: max. diam./min. dia. ratio=1:1.08) was previously rinsed, dried and, then, dipped into the above solution at a carbon-to-solution ratio of 1 to 3. The coated carbon was recovered by filtration, dried in a current of air and, then, dried at 80° C. overnight. The carbon was further heat-treated at 120° C. for 1 hour, after which it was washed well in boiling water. Comparative evaluations of adsorptive capacity and formation of micro-particles were conducted with this adsorbent and the following three control adsorbents: Control 1: Bead activated carbon of the above description which was washed well with boiling water but left uncoated; Control 2: Bead activated carbon of the same description which was coated with hydroxyethyl methacrylate homopolymer; Control 3: Coconut shell carbon as used in the hemoperfusion column HAEMOCOL ® of Sandev Limited (T. J. Smith & Nephew Ltd.).

(i) Adsorptive Capacity

To 100 ml of an aqueous solution of creatinine (initial conc. 0.2 g/l or inulin (initial conc. 1 g/l) was added 5 g of the adsorbent being evaluated and the mixture was shaken at 37° C. and 100 cycles per min. The change with time in concentration of the solute in the fluid was investigated. The bead carbon coated with hydroxyethyl methacrylate-glycidyl methacrylate copolymer (Example 1) adsorbed and removed 99% or more of creatinine from the fluid in 2 hours, just as did the uncoated bead carbon (Control 1) and the bead carbon coated with hydroxyethyl methacrylate homopolymer (Control 2), while coconut shell carbon (Control 3) adsorbed only about 85%.

The adsorbents of Example 1 and Controls 1 and 2 adsorbed and removed at least 40% of the inulin from the fluid in two hours; whereas, Control 3 adsorbed less than about 5%.

(ii) Formation of micro-particles 5 g of the adsorbent being evaluated was shaken with 10 ml of water at 37° C. and a frequency of 100 cycles per min. for three hours and the supernatant fluid was examined for turbidity. The coconut shell carbon (Control 3) produced a large number of micro-particles as visually ascertained, and the uncoated bead carbon (Control 1) produced a small amount of micro-particles. With the bead carbon coated with hydroxyethyl methacrylate homopolymer (Control 2) and the bead carbon coated with hydroxyethyl methacrylate-glycidyl methacrylate copolymer (Example 1), the presence of micro-particles could not be observed with the naked eye. The ultraviolet-visible absorbance of the supernatant fluids from the three samples as shown in Table 1 below, indicated that the bead carbon coated with glycidyl methacrylate-containing copolymer (Example 1) gives a very low absorbance, due to the presence of very few light-scattering particles.

An electron-microscopic examination of the evaporation residues from these supernatants showed that the uncoated bead carbon (Control 1) revealed the presence of a large number of particles in a broad range of particle size distribution and that, in the case of the bead carbon coated with the hydroxyethyl methacrylate homopolymer (Control 2), the number of particles of the order of 0.1μ in diameter was fairly large, i.e. about twice the corresponding count of the blank (distilled water for injection). The bead carbon coated with glycidyl methacrylate-containing copolymer (Example 1) exhibited particles of the order of 0.1μ which were almost comparable in number to that of the same blank.

Table 1

THE INCIDENCE OF MICRO-PARTICLES (5 g OF ADSORBENT WAS SHAKEN WITH 10 ml OF WATER AT 37° C. and 100 CYCLES/MIN. FOR 3 HOURS, AND THE ABSORBANCE OF THE SUPERNATANT FLUID WAS MEASURED.)

| Sample | 300 nm | 500 nm | 700 nm |
| --- | --- | --- | --- |
| Coated bead carbon of Example 1 (coated with hydroxyethyl methacrylate-glycidyl methacrylate copolymer) | 0.008 | 0.005 | 0.005 |
| Control example 1 (uncoated bead carbon) | 0.143 | 0.128 | 0.117 |
| Control example 2 (carbon coated with hydroxyethyl | 0.021 | 0.015 | 0.012 |

Table 1-continued

THE INCIDENCE OF MICRO-PARTICLES (5 g OF ADSORBENT WAS SHAKEN WITH 10 ml OF WATER AT 37° C. and 100 CYCLES/MIN. FOR 3 HOURS, AND THE ABSORBANCE OF THE SUPERNATANT FLUID WAS MEASURED.)

| Sample | 300 nm | 500 nm | 700 nm |
|---|---|---|---|
| methacrylate homopolymer) | | | |

EXAMPLE 2

The bead carbon coated with hydroxyethyl methacrylate-glycidyl methacrylate copolymer as obtained in Example 1 was packed into a cylindrical column having a capacity of 500 cm$^3$ and the column was connected to an artery and a vein of a dog, both kidneys of which had been removed on the immediately preceding day. Blood was allowed to flow through the apparatus at a rate of 200 ml/min. for 3 hours. The result showed that the creatinine concentration dropped from 3.7 mg % to 0.7 mg %, attesting to the effectiveness of this adsorptive hemoperfusion. Throughout the test period, there was no evidence whatever of clotting or hemolysis. This dog was sacrificed and autopsied. The autopsy revealed no deposits of micro-particles or other foreign matter in the liver, lungs and other organs.

EXAMPLE 3 AND CONTROL EXAMPLE 4

Bead activated carbon similar to that used in Example 1 was coated with a hydroxyethyl methacrylate-glycidyl methacrylate copolymer produced in the same manner as Example 1 except that hydroxyethyl methacrylate and glycidyl methacrylate were used in a ratio of 99:1 by weight. The coated carbon adsorbent was rinsed and dried. This carbon adsorbent was subjected to the follwing test, together with the bead carbon of Control 2 (coated with a hydroxyethyl methacrylate homopolymer, rinsed and dried) and the bead carbon of control 4 (coated with 0.5% collodion solution in ethanol-ether mixture solvent, rinsed and dried). To 40 g of each of the above adsorbents to be evaluated was added 80 ml of water. The resulting mixture was sterilized in an autoclave sterilizer at 120° C. for 20 minutes. After cooling, 10 ml of water was taken from each sample and boiled with 20 ml of a 0.01 N aqueous solution of KMnO$_4$ and 1 ml of dilute sulfuric acid for 3 minutes. After cooling, 0.1 g of KI and 5 drops of a starch reagent were added and a titration was carried out with a 0.01 N aqueous solution of Na$_2$S$_2$O$_3$. As a blank, 10 ml of water was similarly treated. The respective KMnO$_4$ consumptions of the eluates from each bead carbon is shown in Table 2 below.

Table 2

| Sample | KMnO$_4$ Consumption (difference from blank) |
|---|---|
| Example 3: Bead carbon coated with hydroxyethyl methacrylate-glycidyl methacrylate copolymer | 0.4 ml |
| Control Example 2: Bead carbon coated with hydroxyethyl methacrylate homopolymer | 2.2 ml |
| Control Example 4: Bead carbon coated with collodion | 9.9 ml |

EXAMPLE 4

In a beaker, 300 g of the same activated carbon (BAC-MU.L manufactured by Taiyo Kaken K.K.) coated with hydroxyethyl methacrylate-glycidyl methacrylate copolymer as used in Example 3 was immersed in 500 ml of physiological saline and boiled for 10 minutes. After cooling, the adsorbent and saline together were gently poured into a glass cylindrical column of 500 ml capacity, with care being taken to avoid bubbling. After the column was closed, it was placed in an autoclave and sterilized at 120° C. for 20 minutes. After this sterilization procedure, the carbon adsorbents showed no deposit of air bubbles.

CONTROL EXAMPLE 5

The same coated carbon adsorbants as used in Example 4 were immersed in physiological saline previously boiled, defoamed and cooled, at room temperature with occasional stirring for 30 minutes. Thereafter, the slurry was poured into a column similar to that described in Example 4 and sterilized by autoclaving, also as described above. Upon removal from the autoclave, the bead carbon adsorbents showed a number of air bubbles on the surface thereof which bubbles could not be substantially removed by a flow of physiological saline while the column was vibrated. Thus, the carbon adsorbent could not be used for hemoperfusion purposes.

CONTROL EXAMPLE 6

A coated bead carbon adsorbent, prepared as in Example 4, was packed dry into a column and sterilized by autoclaving (120° C.×20 min.). After cooling, physiological saline was passed through the column by means of a roller pump but this procedure failed to remove the air bubbles from the carbon beads.

CONTROL EXAMPLE 7

A coated carbon adsorbent was packed dry into a column as in Control Example 6 and the column was decompressed for an hour by a vacuum pump connected to it. Then, the tube connected to the column was cut in physiological saline which had been previously boiled, defoamed and cooled, so that the saline found its way into the column. Although no bubbles were found within the column at that time, the carbon adsorbent showed the presence of air bubbles after 20 minutes' autoclave sterilization at 120° C. This indicates that purging with a vacuum-pump cannot completely remove the gas adsorbed within the carbon and that the residual gas causes the formation of air bubbles on the surface of the carbon in the course of autoclave sterilization.

What is claimed is:

1. A hemoperfusion adsorbent comprising an adsorbent material containing at least one coating thereon of a hydrophilic polymer prepared by the polymerization of at least one monomeric acrylate or methacrylate represented by the formula:

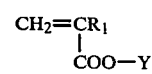

wherein Y is a radical selected from the group consisting of —R$_2$—OR$_3$ and —R$_2$—NR$_3$R'$_3$, R$_1$ is hydrogen or methyl, R$_2$ is a divalent alkylene radical containing 2 to 3 carbon atoms or a poly(oxyalkylene) radical, and $R_3$ and $R'_3$, respectively, are hydrogen or an alkyl group containing 1 to 3 carbon atoms which can be substituted with polar radicals, with a copolymerizable monomer containing an epoxy moiety therein represented by the formula:

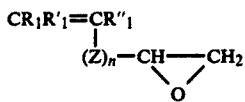

wherein Z is a divalent radical selected from the group consisting of $-COO-R_2-$ and $-CH_2-OCH_2-$, n is 0 or 1, $R_1$, $R'_1$ and $R''_1$ are each, respectively, hydrogen or methyl and $R_2$ is a divalent alkylene radical containing 1 to 3 carbon atoms or a poly(oxyalkylene) radical, wherein the feed ratio of the copolymerizable monomer containing an epoxy moiety therein in the polymerization ranges from 0.1 to 10% based on the weight of total monomers.

2. A hemoperfusion adsorbent as defined in claim 1 wherein the adsorbent material comprises adsorbent particles having a diameter from about 0.1 to 5 mm.

3. A hemoperfusion adsorbent as defined in claim 2 wherein the adsorbent is activated carbon.

4. A hemoperfusion adsorbent as defined in claim 3 wherein the activated carbon is bead activated carbon manufactured from petroleum pitch.

5. The heat cured hemoperfusion adsorbent of claim 1.

6. A hemoperfusion adsorbent as defined in claim 1 which has been substantially freed from air bubbles by boiling said adsorbent in water or physiological saline, cooling said adsorbents, packing said adsorbents into a container and sterilizing the packed container by autoclaving.

7. A hemoperfusion adsorbent as defined in claim 6 wherein sterilization is effected by introducing water vapor into the autoclave at a temperature of at least 120° C.